United States Patent
Cho et al.

(10) Patent No.: US 6,692,517 B2
(45) Date of Patent: *Feb. 17, 2004

(54) OPTICAL RADIATION TREATMENT FOR ENHANCEMENT OF WOUND HEALING

(75) Inventors: George Cho, Hopkinton, MA (US); Horace Furumoto, Willesley, MA (US); Rafael A Sierra, Palmer, MA (US)

(73) Assignee: Cynosure, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/828,996

(22) Filed: Apr. 9, 2001

(65) Prior Publication Data

US 2002/0004673 A1 Jan. 10, 2002

Related U.S. Application Data

(63) Continuation-in-part of application No. 09/804,491, filed on Mar. 12, 2001, now abandoned, which is a continuation of application No. 09/231,746, filed on Jan. 15, 1999, now Pat. No. 6,210,426.

(51) Int. Cl.$^7$ .............................................. A61N 00/00
(52) U.S. Cl. ............................. 607/88; 607/89; 606/3; 606/8; 128/898
(58) Field of Search ...................... 606/3, 8, 9; 607/88, 607/89; 128/898

(56) References Cited

U.S. PATENT DOCUMENTS

| | | | | | |
|---|---|---|---|---|---|
| 4,672,969 A | * | 6/1987 | Dew | .......................... | 128/397 |
| 5,464,436 A | * | 11/1995 | Smith | .......................... | 607/89 |
| 5,766,233 A | * | 6/1998 | Thiberg | ........................ | 607/88 |
| 5,897,549 A | * | 4/1999 | Tankovich | .................... | 606/98 |
| 5,951,596 A | * | 9/1999 | Bellinger | ...................... | 607/89 |
| 5,964,749 A | * | 10/1999 | Eckhouse et al. | ............... | 606/9 |
| 6,027,495 A | * | 2/2000 | Miller | ........................... | 606/9 |
| 6,086,580 A | * | 7/2000 | Mordon et al. | ................. | 606/9 |
| 6,210,426 B1 | * | 4/2001 | Cho et al. | ..................... | 607/89 |
| 2002/0087207 A1 | * | 7/2002 | Cho et al. | ..................... | 607/89 |

* cited by examiner

Primary Examiner—Linda C. M. Dvorak
Assistant Examiner—Ahmed M Farah
(74) Attorney, Agent, or Firm—Don Halgren

(57) ABSTRACT

A method for the reduction in healing time for a wound on the skin of a mammalian patient. The method comprises the steps of providing an optical radiation apparatus with a handpiece communicating therewith, energyzing the optical radiation apparatus to provide a beam of light, and directing the light beam onto a wound or surgical site of a patient. The beam has a wavelength range of about 530 nm to 1000 nm and the beam has a fluence range of from 2 J/cm$^2$ to 5 J/cm$^2$. The beam is preferably generated by a pulse dye laser apparatus.

5 Claims, 1 Drawing Sheet

OPTICAL RADIATION TREATMENT FOR ENHANCEMENT OF WOUND HEALING

This application is a continuation-in-part application of my earlier application Ser. No. 09/804,491, filed Mar. 12, 2001 now abandoned, which application is a continuation of my application Ser. No. 09/231,746, filed Jan. 15, 1999, now U.S. Pat. No. 6,210,426, all of which are incorporated herein by reference, in their entirety.

BACKGROUND OF THE INVENTION

1. Field of the Invention

This invention relates to laser treatment arrangements, and more particularly to a laser system for enhancing the healing of wounds on mammalian tissue.

2. Prior Art

Wounds are a fact of life for most people at one time or another. Such wounds may arise as a result of an accident, injury, or surgical procedure. Healing of a wound will begin immediately. The healing process may take a week to a month, depending upon the severity of the skin injury. In an injury where blood vessels are severed along with the dermis and epidermis layers of the skin, the red and white blood cells from those severed vessels leak into the wound site. The blood cells which are called platelets "thrombocytes", and a blood-clotting protein called fibrinogen, help form a clot of the blood. The cells begin to form a network, and the sides of the injury begin to join together. Cellular debris from the epidermis layer begins to invade the area amongst the blood cells. Fibroblasts, or the tissue forming cells, close in around the injury. Within twenty-four hours, the injured or clotted area becomes dehydrated, and a scab is formed at the site. Neutrophils or white blood cells travel from the blood vessels into the injured area and ingest microorganisms, cellular debris, and other foreign material. Division of the epidermal cells begins at the edge of the injury, and those cells begin to build a bridge across that tissue wound. Monocytes, or white blood cells, migrate toward the wound from its surrounding tissue.

Monocytes enter the wound site itself within two to three days after the wound or surgical procedure site was created. Those monocytes ingest the remaining foreign material. The epidermal cells complete a patch of new skin under the scab that is formed. After a new epidermal surface has been formed, the protective scab is sloughed off. Then the tissue forming cells called fibroblasts begin to build scar tissue on the wound, with collagen.

The epidermis has been restored after about ten days from the injury or surgical procedure, and the scab is typically gone. A tough wound scar tissue may continue to build up, and bundles of collagen accrue along the lines of the original wound injury or surgical cut.

It is an object of the present invention to provide a unique wound treatment aimed at stimulating collagen production together with other growth factors to heal a wound more quickly.

It is a further object of the present invention to provide an efficient cost effective treatment for mammalian wounds due to accidents or surgical procedures, aimed at enhancing or shortening the period necessary for the healing process of that wound.

BRIEF SUMMARY OF THE INVENTION

The present invention comprises an arrangement for the enhancement of the healing process of a wound or a surgical site. The healing process is accomplished by the use of an optical radiation apparatus such as a pulse dye laser. The pulse dye laser is connected to a handpiece by an elongated flexible optical fiber. The laser handpiece is connected at the distal end of the elongated flexible optical fiber and includes a lens or lenses for forming a beam of light directable towards a surgical wound or a site of an injury. The apparatus of the present invention creates a beam of light preferably having a wavelength range of between about 530 nm to about 1000 nm. The beam of optical radiation of the present invention preferably has range of pulse width between about 0.1 ms. to 100.0 ms. The fluence of the laser may extend from a range of about 2 $J/cm^2$ to about 5 $J/cm^2$. Such a laser pulse is intended to enhance or minimize the time for the wound healing process by stimulating its rate of collagen production from the fibroblast together with other growth factors such as epidermal, platelet-derived fibroblasts and transforming growth factors-beta, for skin repair.

The method of operating the optical radiation apparatus of the present invention includes the application of the optical radiation of wavelength range between about 530 nm and 1000 nm, with a pulse width in a range of about 0.1 ms to 100.0 ms onto the site of an injury of surgical procedure of a patient. The wound may be fresh, or old and un-healed. It may also be ulcerous or have sores caused by disease conditions such as diabetes or it may be caused by a patient being bed-ridden for a prolonged period.

It is thus appreciated that the utilization of the optical radiation apparatus of the present invention with a wave length range of between about 530 nm and 1000 nm, and a fluence of about 2 $J/cm^2$ to about 5 $J/cm^2$ may enhance wound healing.

The invention thus comprises a method for the enhancement of wound healing on the skin of a patient after the beginning healing of a wound or surgical site, comprising the steps of: providing an optical radiation apparatus with an optical radiation handpiece communicating therewith; energyzing the optical radiation apparatus, to provide a beam of light through the handpiece; and directing the beam from the handpiece onto a wound or surgical site. The method may also include the beam of light having a wavelength range of about 530 nm to about 1000 nm. The method also includes the beam having a fluence range of from 2 $J/cm^2$ to 5 $J/cm^2$. The pulse dye laser beam also has a beam size of about 3 mm to about 10 mm in diameter.

The invention may also comprise a method for enhancement of wound healing on the skin of a mammalian patient after the beginning healing of a wound or surgical site, comprising the steps of: providing a pulse dye laser apparatus with a laser handpiece communicating therewith; energyzing the pulsed dye laser apparatus to provide a beam of laser light; directing the laser beam onto a wound or surgical site, wherein the pulse dye laser beam preferably has a wavelength range of about 575 nm to about 600 nm., the pulse dye laser beam having a fluence range of form 2 $J/cm^2$ to 5 $J/cm^2$, the pulse dye laser beam having a pulse width range of about 0.1 ms to 100 ms, and wherein the pulse dye laser beam has a beam size range of about 3 mm to about 10 mm in diameter.

BRIEF DESCRIPTION OF THE DRAWINGS

The objects and advantages of the present invention will become more apparent when viewed in conjunction with the following drawing, in which.

DESCRIPTION OF THE PREFERRED EMBODIMENTS

Figure 1:
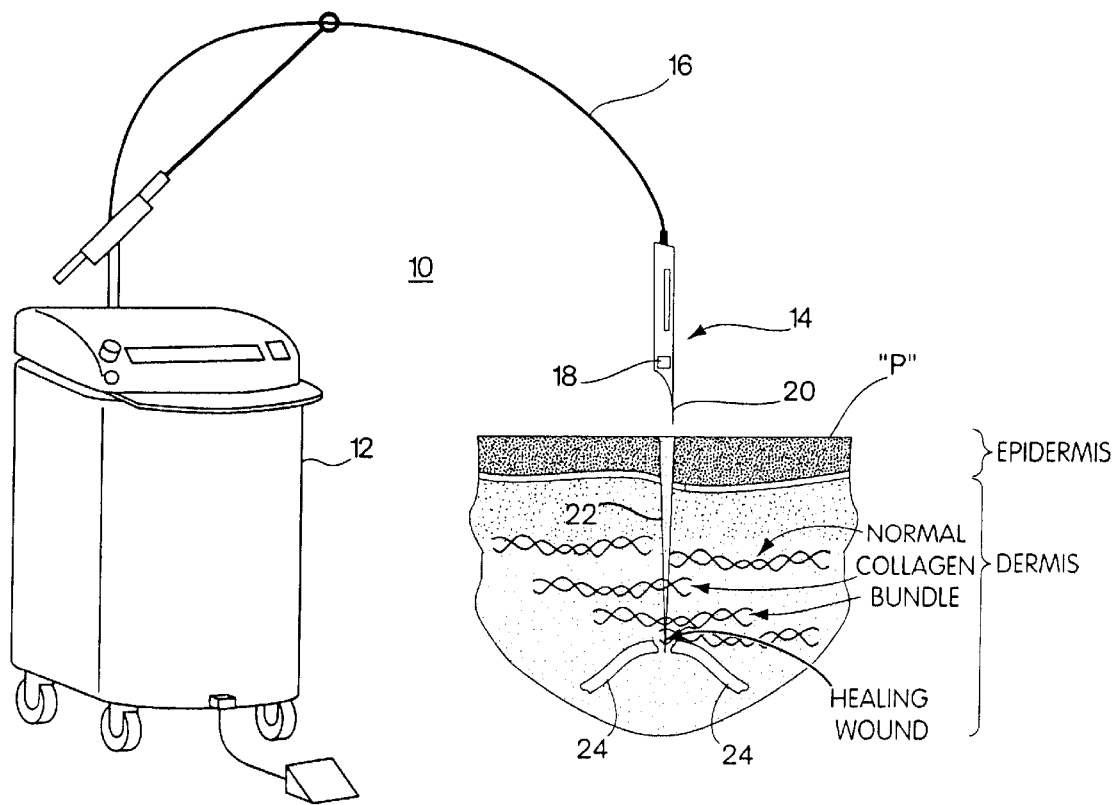
FIG. 1 is a schematic representation of an optical radiation apparatus and an appropriate handpiece directed towards a wound site on a patient, which wound site is shown in cross-section.

Referring now to the drawings in detail, and particularly to FIG. 1, there is shown the present invention that comprises an arrangement for the enhancement of healing of a wound or a surgical site. The wound treatment is accomplished by the use of an optical radiation apparatus 10 such as a pulse dye laser 12. The pulse dye laser 12 is connected to a laser handpiece 14 by an elongated flexible optical fiber 16. The laser handpiece 14 is connected to the distal end of the elongated flexible optical fiber 16 and includes a lens or lenses 18 for forming and directing a beam/pulse of laser light 20 to a surgical wound or a site of an injury 22 on the skin of a patient "P".

The laser 12 of the present invention creates the beam of light 20 preferably having a wavelength range of about 530 nm to about 1000 nm, but preferably about 585 nm, and a beam size of about 3 mm to 10 mm in diameter. The beam of pulse dye laser of the present invention preferably has pulse width range of about 0.1 ms to about 100 ms. The fluence of the laser 12 may extend from a range of about 2 J/cm$^2$ to about 5 J/cm$^2$ with a beam spot diameter of from about 2 mm to 10 mm. As shown in FIG. 1, such a laser pulse 20 is intended to enhance the wound healing process by stimulating the rate of collagen production from the fibroblast, together with the other growth factors for skin repair.

The method of operating the pulse dye laser in accordance with the principles of the present invention includes the application of a preferred range of the optical laser radiation 20 of 575 nm to 600 nm, with a preferred pulse width range of 0.1 ms to 100 ms, which may be applied to the patient "P" shortly or any time after the date of injury or surgical procedure to foreshorten such healing time required. By targeting the capillaries of the blood vessels 24, which vessels 24 for this procedure, are typically smaller than 0.03 mm, the formation of collagen is enhanced working together with other natural growth factors such as epidermal, platelet-derived fibroblasts and transforming growth factors-beta, to thus enhance wound healing. Additional treatment of the surgical site of injury may be provided by the pulse dye laser 12 at follow-up intervals.

Thus it has been shown that the utilization of the pulse dye laser apparatus 10 generating a laser beam 20 with a preferred range of wave length of from about 575 nm to about 600 nm, with a preferred wave length of about 585 nm, and a pulse width range of about 0.1 ms to about 100 ms, with a preferred pulse width of about 0.5 ms and a fluence of about 2 J/cm$^2$ to about 5 J/cm, may minimize the time required for wound healing.

The invention also includes a method for the enhancement of wound healing on the skin of a patient, comprising the steps of providing an optical radiation apparatus 10 with a handpiece 14 communicating therewith, energyzing the optical radiation apparatus 10 to provide a beam of light 20, directing the light beam 20 onto a wound or surgical site 22, wherein the light beam has a wavelength range of at least about 530 nm with an upper wavelength of no more than about 1000 nm, and the light beam has a fluence range of form 2 J/cm$^2$ to 5 J/cm$^2$. The method includes the steps of maintaining the wavelength of the light beam at about 585 nm, and maintaining the pulse width to a range of 0.1 ms to 100 ms.

The invention also includes a method for the treating a patient "P" with a wound or surgical site in a pre-scarring condition, comprising the steps of providing an optical radiation apparatus 10 with a handpiece 14 communicating therewith, energyzing the optical radiation apparatus 10 to provide a wound treating beam of light 20, directing the light beam onto a wound or surgical site 22 of the patient "P", to prevent the occurrence of scar formation at the wound or procedure site. The light beam is preferably a pulse dye laser beam having a wavelength range of about 530 nm to 1000 nm, and a fluence range of from 2 J/cm$^2$ to 5 J/cm$^2$. The laser beam preferably has a pulse width of about 0.1 ms to 100 ms, and a beam size of about 3 mm to about 10 mm. in diameter.

We claim:

1. A method for the reducing the period required of wound healing on the skin of a patient comprising the steps of:

providing a pulse dye laser apparatus with a laser handpiece communicating therewith;

energyzing said pulse dye laser apparatus to provide a beam of laser light;

directing said pulse dye laser beam onto a wound or surgical site of a patient so as to shorten healing time of the wound of a mammalian patient;

wherein said wavelength of said pulse dye laser beam comprises at least about 575 nm and no more than about 600 nm; wherein said pulse dye laser beam has a fluence of at least about from 2 J/cm$^2$; and wherein said pulse dye laser beam has a fluence of no more than about 5 J/cm$^2$.

2. The method for the enhancement of wound healing on the skin of a patient as recited in claim 1, wherein said pulse dye laser beam has a beam diameter size of at least about 3 mm; and wherein said pulse dye laser has a beam size of no more than about 10 mm in diameter.

3. The method for the enhancement of wound healing on the skin of a patient as recited in claim 1, wherein said pulse dye laser beam has a wavelength of 585 nm.

4. The method for the enhancement of wound on the skin of a patient as recited in claim 3, wherein said pulse dye laser beam has a pulse width of at least about 0.1 ms; and wherein said pulse dye laser has a pulse width of no more than about 100 ms.

5. The method for the enhancement of wound healing on the skin of a patient as recited in claim 3, wherein said pulse dye laser beam has a pulse width of about 0.5 ms.

* * * * *